United States Patent

Goble et al.

[11] Patent Number: 5,314,427
[45] Date of Patent: May 24, 1994

[54] CHANNEL LIGAMENT CLAMP

[76] Inventors: E. Marlowe Goble, 850 E. 1200 North; W. Karl Somers, 651 N. 150 West, both of Logan, Utah 84321

[21] Appl. No.: 959,546

[22] Filed: Oct. 13, 1992

[51] Int. Cl.⁵ .................. A61B 17/56; F16B 15/00
[52] U.S. Cl. .......................... 606/72; 606/75; 411/457
[58] Field of Search .......... 606/72, 73, 74, 75, 606/151, 154; 623/13, 16; 411/457, 458, 459, 460, 469, 470

[56] References Cited

U.S. PATENT DOCUMENTS

| | | |
|---|---|---|
| 82,181 | 9/1868 | Tileston . |
| 431,175 | 7/1890 | Southwick . |
| 758,881 | 5/1904 | Yost .................................. 411/457 |
| 1,425,199 | 8/1922 | Hartley . |
| 1,598,026 | 8/1926 | Thompson . |
| 1,638,477 | 8/1927 | Dyer .................................. 411/470 |
| 1,948,462 | 12/1936 | Le Page . |
| 2,065,325 | 12/1936 | Calhoun .......................... 411/457 |
| 2,134,765 | 3/1933 | Putnam . |
| 2,398,603 | 4/1946 | Soderberg . |
| 4,047,524 | 9/1977 | Hall .................................. 606/61 |
| 4,146,022 | 3/1979 | Johnson ..................... 128/92 YD |
| 4,263,903 | 4/1981 | Griggs . |
| 4,278,091 | 7/1981 | Borzone . |
| 4,400,833 | 8/1983 | Kurland . |
| 4,414,967 | 11/1983 | Shapiro . |
| 4,438,769 | 3/1984 | Pratt ............................... 128/924 C |
| 4,456,006 | 6/1984 | Wevers .......................... 128/924 C |
| 4,590,928 | 5/1986 | Hunt et al. . |
| 4,592,346 | 6/1986 | Jurgutis . |
| 4,632,100 | 12/1986 | Somers et al. . |
| 4,659,604 | 4/1987 | Lambuth . |
| 4,711,234 | 12/1987 | Vives et al. . |
| 4,738,255 | 4/1988 | Goble et al. . |
| 4,793,335 | 12/1988 | Frey ................................. 623/13 |
| 4,960,420 | 10/1990 | Goble ................................ 606/72 |
| 4,988,351 | 1/1991 | Paulos et al. . |

Primary Examiner—Michael A. Brown
Attorney, Agent, or Firm—M. Reid Russell

[57] ABSTRACT

The improved channel ligament clamp of the invention is for human implantation in a surgical procedure for securing a ligament, that is either natural or prosthetic, onto a bone cortex and includes, as a clamp body, a rectangular section of a thin, flat metal material, such as titanium, with identical equal opposite edge portions of which material bent at approximately right angles forming upstanding parallel side walls. Edges of which upstanding parallel side walls are for contacting a bone surface whereto the clamp is secured to closely contain a ligament section therebetween without crushing it, and which parallel side walls are the side walls of a channel section with the flat material therebetween constituting the channel section web. Which channel section web includes a plurality of pointed end parallel pins secured thereto that extend at right angles and are parallel to clamp the side walls. Preferably four pins are employed with each arranged as a corner of a square pattern, and a hole that is preferably threaded, is formed through the web in the center of which formed square for passing a screw type connector therethrough.

4 Claims, 1 Drawing Sheet

CHANNEL LIGAMENT CLAMP

BACKGROUND OF THE INVENTION

1. Field of the Invention

This invention relates to devices and arrangements for securing a ligament, or the like, to a bone surface during a ligament repair or replacement surgical procedure.

2. Prior Art

The present inventors are inventors of an earlier invention entitled, Channel Ligament Clamp and System, U. S. Pat. No. 4,960,420, that shows an earlier channel ligament clamp. Which earlier clamp employs spikes as channel sides with a web extending therebetween wherefrom spaced parallel pins extend at right or normal angles and are parallel to which spikes. The improved clamp of the present invention employs continuous short side walls rather than spikes as channel sides. With the clamp installed, the short side walls of the clamp of the invention, contacts the bone surface to contain a ligament without crushing it. The improved clamp is installed by driving the parallel pins through a ligament and into holes prepared in a bone surface and turning a screw through a web hole and into which bone surface.

Prior to channel ligament clamp type systems, staple arrangements were commonly employed in ligament repair and replacement surgical procedures for attaching a ligament to a bone surface. Examples of such staple devices for medical applications are shown in patents to Hall, U.S. Pat. No. 4,047,524; to Johnson, et al, U.S. Pat. No. 4,146,022; to Griggs, U.S. Pat. No. 4,263,903; to Borzone, U.S. Pat. No. 4,278,091; to Kurland, U.S. Pat. No. 4,400,833; to Shapiro, U.S. Pat. No. 4,414,967; to Pratt, et al, U.S. Pat. No. 4,438,769; and to Wevers, et al, U.S. Pat. No. 4,456,006. All of which staple devices provide for fitting the staple like device across the ligament to secure the ligament between the staple legs by driving it into the bone surface. None of which devices, however are like the clamp of the present invention. Additionally, while a number of staple and staple like devices common to wood working are available, none are structurally or functionally like the device of the present invention. Examples of such wood working devices are shown in early patents to Tileston, U.S. Pat. No. 82,181; to Southwick, U.S. Pat. No. 431,175; to Yost, U.S. Pat. No. 758,881; to Hartley, U.S. Pat. No. 1,425,199; to Thompson, U.S. Pat. No. 1,598,026; to Dyer, U.S. Pat. No. 1,638,477; to Le Page, U.S. Pat. No. 1,948,462; to Putnam, U.S Pat. No. 2,134,765; to Soderberg, U.S. Pat. No. 2,398,603; and in a later patent to Lambuth, U.S. Pat. No. 4,659,604.

Some examples of other devices for connecting ligament ends to a bone surface or within a bone are shown in a patent to Hunt, et al, U.S. Pat. No. 4,590,928 and in patents that the present inventors are inventors of, U.S. Pat. Nos. 4,632,100 and 4,738,255. Also patents to Vives, et al, U.S. Pat. No. 4,711,234 and to Paulos, et al, U.S. Pat. No. 4,988,351, show, respectively, pin and disk couplings for ligament mounting to a bone mass, and devices for mounting a ligament to a bone surface are shown in patents to Jurgutis, U.S. Pat. No. 4,592,346 and to Frey, et al, U.S. Pat. No. 4,793,335 that show multi-pin staple arrangements. None of which connector and staple configurations, however, involve a channel structure with the short ligament containing side walls like the ligament mounting device of the present invention.

BRIEF SUMMARY OF THE INVENTION

It is a principal object of the present invention in an improved channel ligament clamp to provide a device for mounting a ligament onto a bone surface such that the ligament material will be contained between the clamp side walls.

Another object of the present invention is to provide an improved channel ligament clamp having a flat web between short parallel ligament retaining side walls that are of a height such that, with the side wall edges in contact with a bone surface, a ligament contained therebetween will be tightly clamped but not crushed by the web undersurface.

Another object of the present invention is to provide an improved channel ligament clamp where the web includes a plurality of sharp ended parallel pins that extend from the web undersurface for driving through a ligament and into a bone surface or into preformed holes in a bone surface.

Still another object of the present invention is to provide an improved channel ligament clamp that, when positioned over a ligament fitted onto a bone surface, is easily secured thereto by fitting a single screw type fastener through a hole formed through the web to pierce the ligament and turning it into the bone.

Still another object of the present invention is to provide an improved channel ligament clamp that is easily and accurately positioned over a ligament at a bone surface location, and is retained thereat by turning a single screw type fastener through the hole, captured ligament, and into the bone to provide a reliable and secure ligament to bone surface mounting.

The improved channel ligament clamp of the present invention is preferably formed from a flat rectangular section of a human body compatible material, such as, titanium or other material as is appropriate for human implantation. The opposite parallel long side segments of which section of material are bent upwardly at approximately right angles, forming the channel side walls. The channel sides to be equal and of a height to closely contain a thickness of a ligament, with the side wall edges for engaging the surface of a bone whereto a ligament is to be attached. The area between which channel side walls, or web, has a hole formed therethrough for receiving a screw type fastener that travels through a ligament contained between the side walls and is turned into the bone, as a purchase of one bone surface or cortex.

For both positioning the improved channel ligament clamp to the bone to sandwich a ligament therebetween, the web includes a plurality of sharp ended spikes that are parallel to one another and are mounted so as to extend parallel therefrom alongside the channel side walls. Which spikes each have a greater length than the height of the channel side walls so as to penetrate the ligament and travel into the bone surface.

For mounting a ligament onto a bone cortex surface, the ligament location is identified and the improved clamp pin hole locations are preferably pre-drilled. Though, the pin holes can be formed by first positioning the ligament thereover and applying a hammer force onto the clamp web so as to drive which pins into the bone. After the pin holes are formed, the ligament is positioned over the holes and the improved clamp is fitted thereon and the pins urged through the ligament to travel into the drilled pin holes. A fastener, such as a screw, is then fitted through the hole in the clamp web, and turned through the ligament and into the bone, completing the mounting.

DESCRIPTION OF THE DRAWINGS

These and other objects and features of the present invention will become more fully apparent from the following description taken in conjunction with the accompanying drawings.

DETAILED DESCRIPTION

It is generally the case in ligament repair or replacement surgical procedures involving biologic grafts or prosthetic ligaments that the ligament end must be exactly positioned and maintained onto a bone surface or cortex location. Once proper ligament positioning is determined a fastener device is used to attach the ligament end to that bone surface location, which ligament is usually under tension. The need for exact positioning of a ligament while maintaining proper ligament tensioning is obviously difficult. This difficulty is minimized utilizing the improved channel ligament clamp 10 of the invention, hereinafter referred to as clamp.

Figure 1:
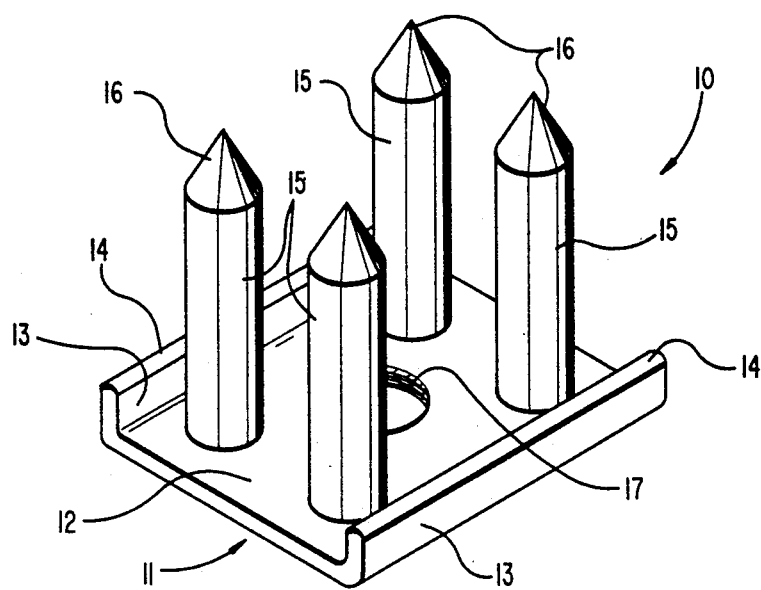
FIG. 1 is a profile perspective view of an improved channel ligament clamp of the invention.
Figure 2:
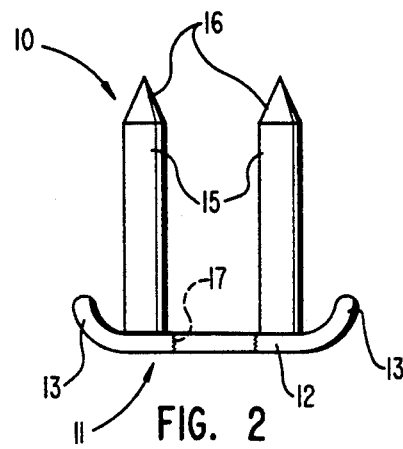
FIG. 2 is an end elevation view of the improved channel ligament clamp of FIG. 1.

Clamp 10, shown in FIGS. 1-4, is for securing a ligament end, not shown, under tension onto a bone surface. The clamp 10, from the end view of FIG. 2, is shown as having a flat channel body portion 11 that includes a flat thin web 12 with sides that are equally upturned, at right angles, along opposite web edges, forming short upstanding parallel side walls 13. The short upstanding parallel side walls 13, hereinafter referred to as side walls that, when the edges thereof are in contact with a bone surface, are of a height that is appropriate to clamp and contain a ligament therebetween without crushing it. During clamp installation, as the web 12 is moved against the ligament, squeezing it tightly against a bone surface, the side walls 13 prohibit ligament material from extruding out from under flat wall edges 14. Which flat wall edges 14 engage the bone surface along their lengths when the clamp is installed onto a bone surface.

As shown, the clamp 10 includes a plurality of parallel outstanding pins 15, each having a sharp pointed end 16. The pins 15, are shown herein as four pins grouped in a square. Within which square a threaded opening 17 is formed through the center of web 12. The pins 15 are either formed as integral parts of the clamp in the fabrication process, or are separately formed and may be installed, as by individually stacking each pin in the web, or by like method within the scope of this disclosure. Which clamp web 12, as shown best in FIG. 1, is preferably square though, of course, it could be rectangular, or another shape within the scope of this disclosure.

Figure 3:
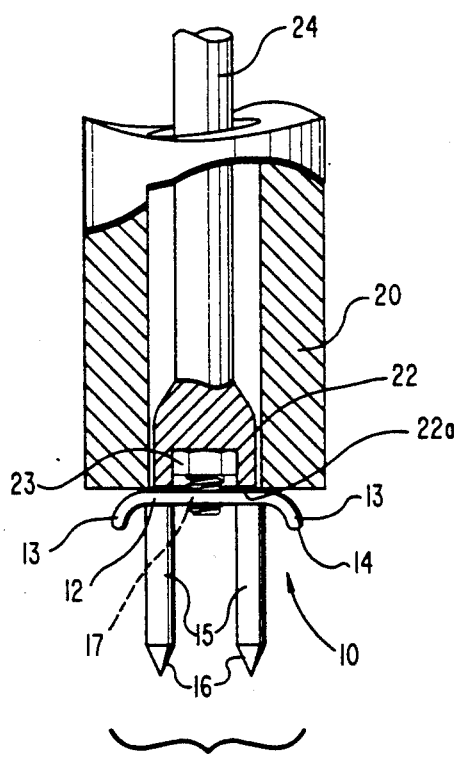
FIG. 3 is a side elevation view of the improved channel ligament clamp of FIG. 1, showing a driver tool body positioned thereabove that has had a section removed exposing a hole or passage from the tool top of curved undersurface, through which hole or passage a bolt is fitted to the end of a socket type turning tool is fitted and turned into a threaded hole in the improved channel ligament clamp web for mounting the clamp to the driver tool.
Figure 4:
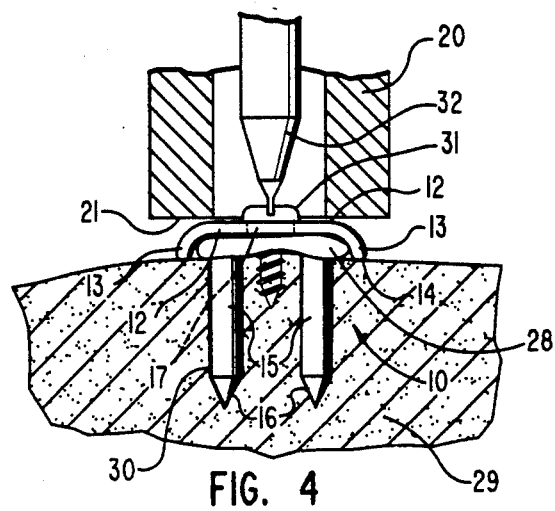
FIG. 4 is an end view of the improved channel ligament clamp fitted over a ligament on a bone surface with a screw shown in solid and broken lines being turned through the clamp and ligament and seating in the bone.

For securing a ligament end onto a bone cortex 29, shown in FIG. 4, ligament positioning is determined and that selected location marked appropriately. At that location a template, or the like, wherethrough a pattern of holes in the arrangement of pins 15 is positioned. Holes 30, illustrated in FIG. 4, that reproduce the arrangement of pins 15 are then formed a distance into the bone to a depth appropriate for seating pin 15 therein. The ligament, under tension, is then positioned over which pattern of holes and the clamp 10 is mounted onto a driver tool 20, as shown in FIG. 3, is aligned. In which alignment, such that the pin 15 sharp ends 16 align with the holes 30 in the pin pointed ends 16 are positioned above which bone 29 holes 30. The clamp pins 15 are then urged through the ligament and individually into the individual bone holes 30. The driver tool 20 that has a flat or curved bottom clamp contacting undersurface 21 to receive and closely fit to the curved top surface of the clamp 10 web 12. A bolt 23 maintained onto the head of a driver 24 is fitted through a straight longitudinal hole or passage 22 formed through which tool body from top to undersurface, passing through a necked in end 22a of which hole or passage, that is of a diameter to pass the threaded bolt 23 body but not the bolt head and is turned into the threaded clamp web hole 17, mounting the clamp 10 onto the driver that is then struck, as with a hammer, to drive the pin sharp ends 16 through the ligament 28 and into the drilled holes 30, as shown in FIG. 4. A screw 31 turned by an end 32 of a screw driver can then be turned through ligament 28 and turned into bone 29, as shown in broken lines, purchasing one cortex.

A preferred procedure for installing a ligament onto the bone 29 cortex utilizing clamp 10 is set out above as involving drilling a pattern of holes 30 in a bone 29 at the selected ligament location prior to fitting the ligament 28 thereover and installing clamp 10, as described. It should, however, be understood, that the bone 29 need not be pre-drilled and that the clamp 10 can be fitted over a positioned ligament 28 and the clamp driven through that ligament and into the bone, without using driver 20, as by striking the top surface of web 12 with a hammer, or like tool, within the scope of this disclosure.

As set out above, the clamp 10 is for human implantation for maintaining ligament 28 onto a bone 29 surface, and accordingly, must be fabricated from a human body compatible material such as titanium, or like material. Also, while the pattern of four pins 15 formed in a square surrounding the threaded web hole 17 is shown as preferred for stabilizing the connection of the clamp to bone that is provided by the single screw 31 type fastener, it should, however, be understood that another appropriate number of pins 15 or pattern of pins for providing a similar clamp 10 to ligament 28 mounting strength as that provided by the four pin 15 arrangement could be so employed within the scope of this disclosure.

While a preferred embodiment of the invention in an improved channel ligament clamp has been shown and described herein, it should be understood that the present disclosure is made by way of example only and that variations to the described structure and tooling, and the clamp installation procedure are possible within the scope of this disclosure without departing from the subject matter coming within the scope of the following claims, and a reasonable equivalency thereof, which claims we regard as our invention.

We claim:

1. A ligament clamp comprising, a thin flat rectangular section of a material that is suitable for human implantation, with the opposite parallel side portions of said section of material bent at approximately right angles to form identical short parallel upstanding side walls, with said parallel side walls and the material therebetween, or web, constituting a channel section, said parallel side walls of said channel section each having a smooth flat bone engaging edge and are each of a height to contain, without crushing a section of a ligament fitted therebetween; a plurality of equal length, spaced apart pointed pins, that extend beyond said parallel side walls, each said pin secured at its base to said web in a pattern to extend parallel at right angles outwardly from said web, and parallel to said side walls; and said web has a threaded hole formed therethrough said pins form an array that surrounds said threaded hole, wherein said pins extend outwardly and from within said walls of said web.

2. A ligament clamp as recited in claim 1, wherein web of the channel section is square; and four pointed pins make up the plurality of pins, with each pointed pin mounted to extend from said web as the corner of a square, and the hole formed through said web is located at the center of said square formed by said pointed pins.

3. A ligament clamp as recited in claim 1, wherein the channel section and pointed pins are formed from titanium.

4. A ligament clamp as recited in claim 1, further including tool means for mounting to the ligament clamp for positioning it onto a bone surface with a section of a ligament contained between the parallel side walls, consisting of a tool body formed as a block of metal that has an undersurface formed for engaging the top surface of the web, said tool body having a straight longitudinal hole formed therethrough from its top to its undersurface for passing a bolt type fastener on the end of a driver therethrough that is turned into the ligament clamp web threaded hole, the driver tool for positioning said ligament clamp over a ligament and is struck to drive the pins through said ligament and into a bone.

* * * * *